(12) United States Patent
Daugirdas

(10) Patent No.: US 7,211,051 B2
(45) Date of Patent: May 1, 2007

(54) REMINDER SYSTEM FOR PERSONAL MEDICAL SAMPLING OR TREATMENT PROCEDURES

(76) Inventor: John T. Daugirdas, 15W560 89th St., Hinsdale, IL (US) 60521

( * ) Notice: Subject to any disclaimer, the term of this patent is extended or adjusted under 35 U.S.C. 154(b) by 623 days.

(21) Appl. No.: 10/386,296

(22) Filed: Mar. 11, 2003

(65) Prior Publication Data

US 2004/0181171 A1   Sep. 16, 2004

(51) Int. Cl.
*A61B 5/00* (2006.01)
*A61B 19/00* (2006.01)

(52) U.S. Cl. ........................... 600/573; 128/898
(58) Field of Classification Search ............... 2/243.1, 2/244, 246; 40/586; 128/897, 898; 600/573, 600/574; 604/317

See application file for complete search history.

(56) References Cited

U.S. PATENT DOCUMENTS

| | | | | |
|---|---|---|---|---|
| 249,777 | A | | 11/1881 | La Fleur .......................... 256/4 |
| 2,739,593 | A | * | 3/1956 | McLaughlin .................. 604/15 |
| 4,179,833 | A | | 12/1979 | Knodel ........................... 40/21 |
| 4,317,454 | A | * | 3/1982 | Bucalo ......................... 600/572 |
| 4,423,734 | A | | 1/1984 | Schawel ...................... 128/460 |
| 4,820,164 | A | | 4/1989 | Kemper ...................... 434/238 |
| 5,046,446 | A | * | 9/1991 | Sumrall et al. ............. 116/200 |
| 5,093,935 | A | * | 3/1992 | Countee, Jr. .................... 2/400 |
| 5,244,096 | A | | 9/1993 | Stoner ......................... 206/581 |
| 5,357,981 | A | | 10/1994 | Eilam et al. ................. 128/848 |
| 5,368,583 | A | * | 11/1994 | Fleury ......................... 604/318 |
| 5,417,674 | A | * | 5/1995 | Smith et al. ................. 604/289 |
| 5,460,188 | A | | 10/1995 | Barrett, Sr. .................. 128/842 |
| 5,487,546 | A | * | 1/1996 | Yasuda ........................ 473/217 |
| 5,606,748 | A | | 3/1997 | Fujiwara ........................ 2/406 |
| 5,718,003 | A | * | 2/1998 | Gwinn ........................... 2/405 |
| 5,842,959 | A | * | 12/1998 | Wilkinson ................... 482/121 |
| 5,894,271 | A | | 4/1999 | Namisniak ............... 340/407.2 |
| 6,017,321 | A | * | 1/2000 | Boone .................... 604/385.18 |
| 6,041,445 | A | | 3/2000 | Davitt ............................ 2/400 |
| 6,253,385 | B1 | * | 7/2001 | Fields ............................ 2/246 |
| 6,312,419 | B1 | * | 11/2001 | Durel-Crain ........... 604/385.18 |
| 6,409,712 | B1 | * | 6/2002 | Dutari .................... 604/385.09 |
| 2004/0082927 | A1 | * | 4/2004 | Littleton et al. ............ 604/346 |
| 2005/0160636 | A1 | * | 7/2005 | Nein et al. ..................... 40/119 |

* cited by examiner

*Primary Examiner*—Max Hindenburg
*Assistant Examiner*—Michael Apanius
(74) *Attorney, Agent, or Firm*—Brown & Michaels, PC

(57) ABSTRACT

A method for reminding an individual to collect a urine specimen includes the steps of providing a pad or clip having a reminder area of a size such that the individual touches and discovers the pad, when preparing to urinate, and attaching the pad to the brief in the groin area, in a location where it will be encountered, and underneath an outer-garment, whereby the pad is hidden from view when in normal use, and whereby the individual, when preparing to urinate, will touch and discover the pad and thereby be reminded to collect the urine specimen. The pad or clip optionally is attached to the fly of a male brief or to the waistband of either a male or female brief. The invention accomplishes the reminder task by way of imposing behavior modification on the user by operating as a forced interruption to an otherwise established routine or ritual.

21 Claims, 4 Drawing Sheets

REMINDER SYSTEM FOR PERSONAL MEDICAL SAMPLING OR TREATMENT PROCEDURES

BACKGROUND OF THE INVENTION

1. Field of the Invention

The invention pertains to the field of information reminding systems. More particularly, the invention relates to the field of personal medical treatment and sample collection reminders.

2. Description of Related Art

An efficacious reminder system is important in certain medical treatments or programs of treatment. This is especially true in regard to the collection of urine specimens.

In medicine, urine is commonly collected for at least three purposes. One purpose is to quantify how much protein is lost in the urine over a 24-hour period. The amount of protein lost directly pertains to whether or not the patient has a serious kidney disease, and 24-hour urine specimens are routinely collected at intervals to monitor the response to treatment of disease that cause protein leakage into the urine.

Another purpose, again utilizing a 24-hour collection time frame, is used to measure the amount of creatinine in the urine. If the 24-hour amount of creatinine in the urine is accurately known, and the creatinine level in the blood also is determined, the functional capacity of the kidney can be determined.

Still another purpose is with patients having renal stones, urine is collected to determine the 24-hour excretion rate of various minerals and other chemicals such as uric acid, calcium, sodium, and citrate.

In all of these instances, the common method is to give the patient a large collection bottle, which may or may not be kept refrigerated, that the patient is sent home with. It is the patient's responsibility to collect all of the urine during the 24-hour period into the bottle. However, a patient normally urinates from 4–8 times over a 24-hour period. Often a patient must use different bathrooms, in his or her house, at work, or other places. During the normal stresses of the day, it is quite easy for a patient to simply go to a bathroom and urinate directly into the toilet, forgetting to collect the sample and thereby causing the collection of urine to be incomplete. This has important consequences. In the case of proteinuria, it can cause the amount of protein leakage to be underestimated, which may lead to an inappropriate diagnosis. In the case of creatinine, the functional capacity of the kidney will be underestimated. In the case of uric acid, calcium, sodium, or citrate, the mineral excretion rate will be underestimated, which may lead to errors in diagnosis and treatment. Collection of urine in children is especially difficult, given their active lifestyles.

The alternative, performing an incomplete urine collection and testing, is by orders of magnitude more costly, since it necessitates repeating every step of the process: another doctor's consultation with a patient; another collection regime requiring another kit; another round of laboratory testing; and, reanalysis of the results, after which the patient may require another consultation. The inconvenience and burden on treatment provider, patient, and overall on the health care system, in addition to the immediate monetary costs, should be evident and can prove very significant.

Devices and reminder systems have previously been provided to remind an individual of certain dates or duties. Some of these systems require an individual to provide input or perform a manual operation of some sort, as for example in the use of visual and handwritten appointment books or electronic calendar devices. Other systems may provide visual or audio aids and features to accomplish a reminder function, examples of which include wristwatch beepers and personal pagers or the like.

U.S. Pat. No. 4,820,164 discloses training pants for a toddler having a releasably attachable pad on the front of the pants containing several figures hidden from view by individual releasable patches of fabric. The figures as such provide a visual reward system for a toddler upon removal of a patch and display of a figure.

U.S. Pat. No. 4,423,734 discloses a nursing bra having an integral reminder device that includes a base member on which is mounted a designating member movable between two indicating positions. The nursing reminder device is not designed to impose behavior modification or to change an established pattern of behavior. Breast-feeding will continue whether or not the nursing bra is employed. The nursing bra simply serves as a marker to identify which of two breasts was last used for feeding.

U.S. Pat. No. 4,179,833 discloses a strap-like band having one or more attached, protruding reminder tabs that attaches to a person's wrist and provides a visual reminder to the wearer.

One disadvantage of prior art reminder devices is that some only provide a visual reminder and therefore can easily remain unnoticed or their presence ignored. Another disadvantage of some prior art reminders is that they are not geared to or suitable for dispensing by primary care providers, such as physicians, physician's assistants, or nurses, to a patient as part of a patient's self-administered specimen collection or treatment kit or activity.

Still another disadvantage of some reminder devices is their relative complexity. This is especially true in regard to electronic devices like electronic handheld calendars/reminders, and is reflected in their relatively higher cost. An additional disadvantage is the requirement that the user input information in order to activate the reminder function. The user must also ensure that the device is working, powered up, not low on charge, and so forth. A disadvantage of watch alarm-type devices is that these provide just a generic reminder without focusing on a specific activity.

SUMMARY OF THE INVENTION

According to the present invention, there is provided a method for reminding an individual to collect a urine specimen that includes the steps of: (a) providing a reminder pad having (i) a reminder area of a size such that the individual will touch and discover the pad in the course of performing a normal bodily function such as urinating, thereby serving as a tactile reminder to collect the specimen, and (ii) a foldable or integral fold portion for attaching the pad to a brief; and (b) attaching the pad to the brief with the foldable or integral fold portion in the groin area. The pad is attached at a location where the individual, when preparing to urinate, will touch and discover the pad and thus be reminded to collect the urine specimen. The reminder area of the pad is positioned under the outer-garment and therefore hidden from view. The invention also includes providing a clip that can be attached to the fly of a male brief or that can be attached to the waistband of a male or female brief.

According to another aspect of the invention, there is provided a method for reminding an individual to either collect a specimen or administer a treatment. The method includes the steps of providing the above-described reminder pad, and attaching the pad to the brief with the foldable or integral fold portion such that the reminder area is positioned at or near the site of collecting the specimen or administering the treatment whereby the individual will touch and discover the pad and thus be reminded to collect the specimen or administer the treatment at that site. Again, the pad is positioned under the outer-garment and therefore hidden from view.

The invention is convenient and easy to use since it merely requires the user to attach the reminder pad to the brief, after which the pad will serve the intended reminder function. The invention provides a tactile reminder that is more effective than just a visual reminder, in that the wearer will touch and discover the pad, and be reminded by its presence of the need to collect the sample or administer the self-treatment and thus avoid interrupting the course of testing or treatment. In this manner, the invention, as opposed to prior art reminder devices, accomplishes the reminder task by way of imposing behavior modification on the user, and by doing so in a manner that might best be categorized as a forced interruption to an otherwise established routine or ritual.

In particular, the reminder pad system helps ensure completeness of a 24-hour (or other time period) collection of urine, because it places an unaccustomed object, the reminder pad, in a place where it must be encountered in the course of normal urination, both for males and females. In the case of males, the reminder system is primarily tactile, as on opening the fly, the soft cardboard disc or pad is encountered. This breaks the automatic ritual or routine nature of urination and jogs the memory that something special must be done at this point; i.e., collect the urine. For women, the disc is encountered on lowering the outer pants or skirt when sitting on the toilet, and the reminder can be both tactile and visual.

The invention is useful for both adults and children, and the reminder function does not rely on just visual cues but is primarily tactile. The reminder pad system would therefore work equally effectively for the sight-impaired. This is a clear-cut advantage over visual-only reminder systems.

The reminder pad further has the further advantage of being very inexpensive. Pads such as cardboard pads can be produced in quantity, and disposable pads can therefore be supplied to the patient along with or as part of a urine collection kit at very low cost.

The reminder pad accordingly helps alleviate the collective costs and burdens on the treatment provider, patient, and indeed the health care system as a whole, that as discussed above can be very significant. The invention is a low cost method of fulfilling an important task and serves important diagnostic and therapeutic functions by enabling the timely completion of tests and evaluations that necessitate self-administered sampling or treatment. The invention can provide important health benefits to a patient by helping to eliminate delay in treatment, by expediting prompt diagnosis and follow-up treatment, and by helping to promote faster and better treatment of illnesses or chronic diseases and the like. The invention accordingly serves to promote more efficient health care and reduce overall health care costs.

DETAILED DESCRIPTION OF THE INVENTION

The personal reminder system and method for collecting a bodily fluid specimen or administering a self-treatment can best be understood by reference to the accompanying drawings and as follows. The terms "individual", "user" and "wearer" in the description that follows are used interchangeably. The terms "self-administer" or "self-treatment" as used herein also include a treatment provider assisting an individual in collecting the specimen or administering the treatment, for example, if a patient is too young, physically handicapped, or for any other reason unable to perform the procedure themselves, as will be made clearer below. The term "brief" as used herein is intended to include both male and female underwear unless noted otherwise. The term "pad" as used herein also includes a clip as is further described below.

Figure 3:
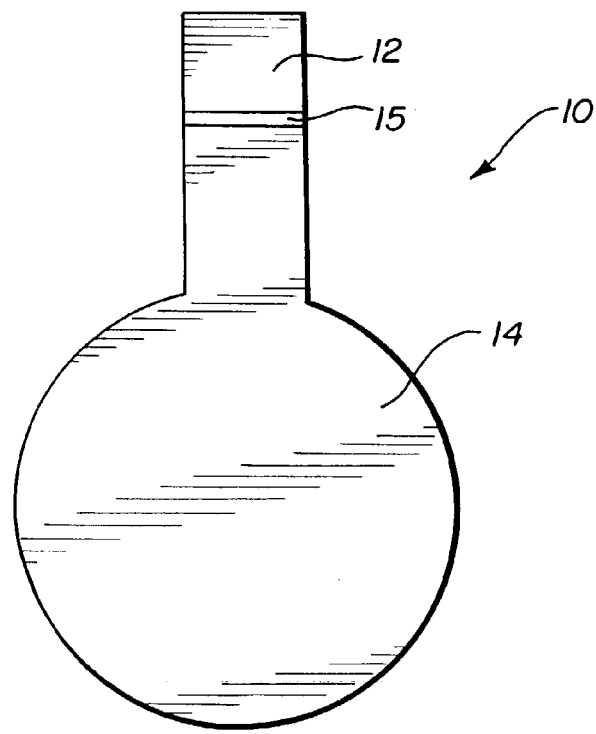
FIG. 3 shows a top plan view of a reminder pad as in the invention.

As illustrated in FIGS. 1–5, reminder pad 10 has a foldable portion, tab 12, and reminder area 14, and as shown in FIG. 3 can have a pre-creased, compressed, or weakened area 15 by which tab 12 can be folded back against pad 10. Pad 10 may therefore be attached by tab 12 to waistband 16. In another embodiment, reminder area 14 of pad or clip 10 may have flared portions 17 such that when attached by tab 12 to waistband 16 of male brief 18 portions 17 overly both sides of vertical fold 21 of brief fly 20. Tab 12 may be preformed and integral with pad 10, for example, as with a one-piece, molded plastic, compression-fit type of pad 10. Pad 10 can also comprise a nickel-sized fold-over clip, such as metal or plastic, that could be attached to vertical fold 21 of fly 20.

Figure 2:
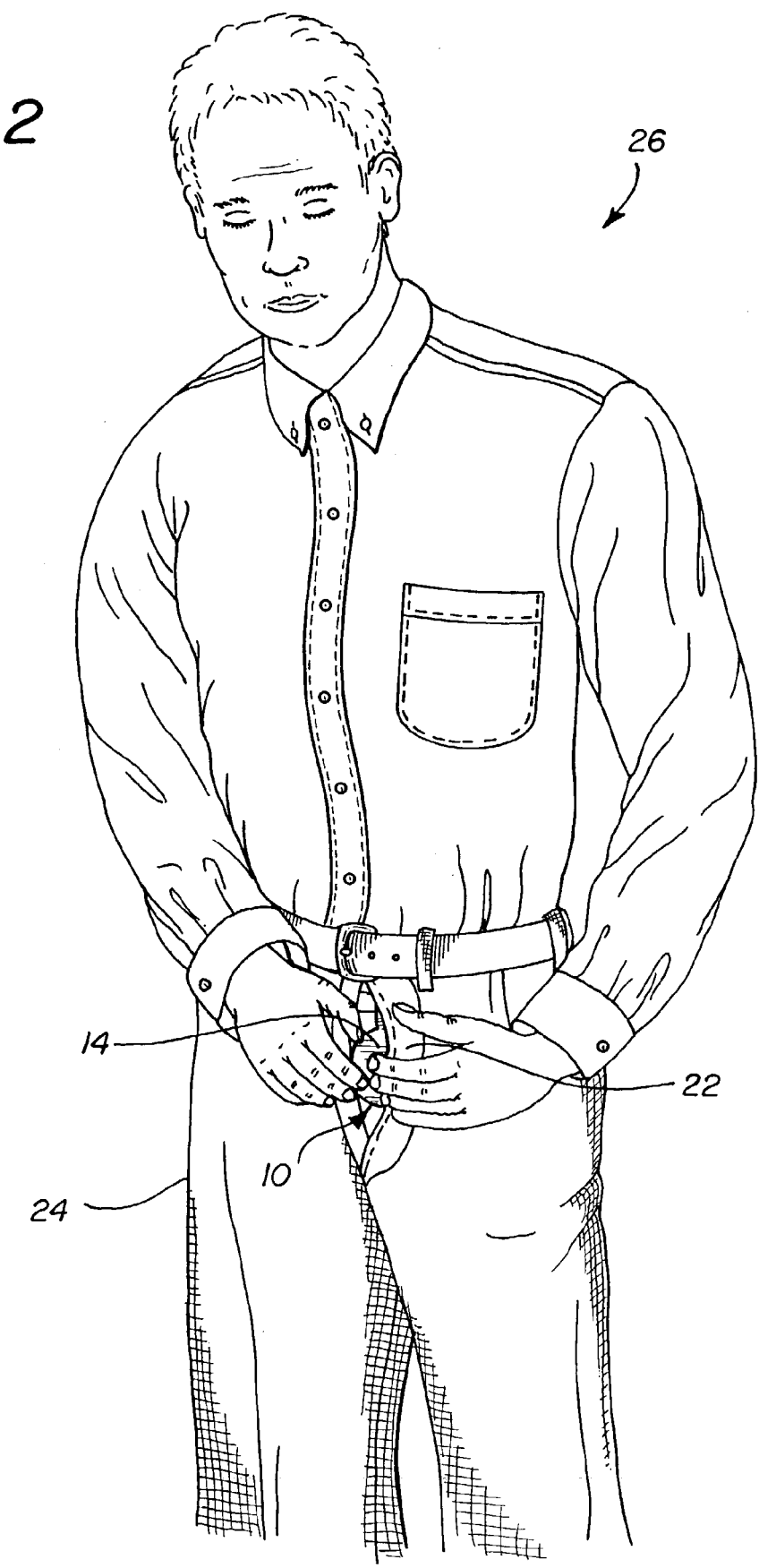
FIG. 2 shows a perspective view of a male wearing a reminder pad as in the invention.
Figure 4:
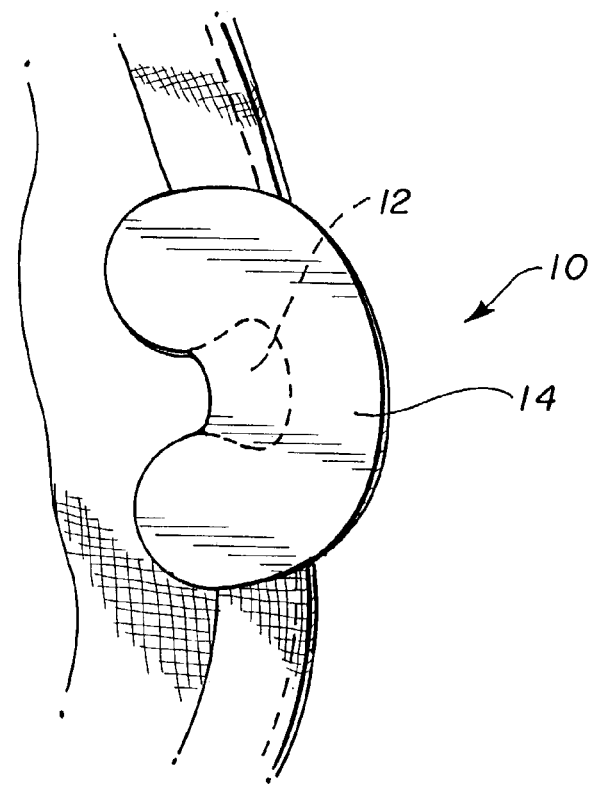
FIG. 4 shows a perspective view of a reminder clip attached to the fly of a male brief as in the invention.

Pad 10 may be positioned either between brief 18 and the wearer's body or between brief 18 and the wearer's outerwear, the latter being illustrated in FIG. 2 where pad 10 is worn between brief 18 and fly 22 of outerwear 24 by male 26. Examples of outerwear 24 for use in the invention for either male or female wearers include but are not limited to trousers, skirts, dresses, pantyhose, or stockings or the like. In any event, pad 10 is hidden from view under outerwear 24 in the practice of the invention.

Figure 6:
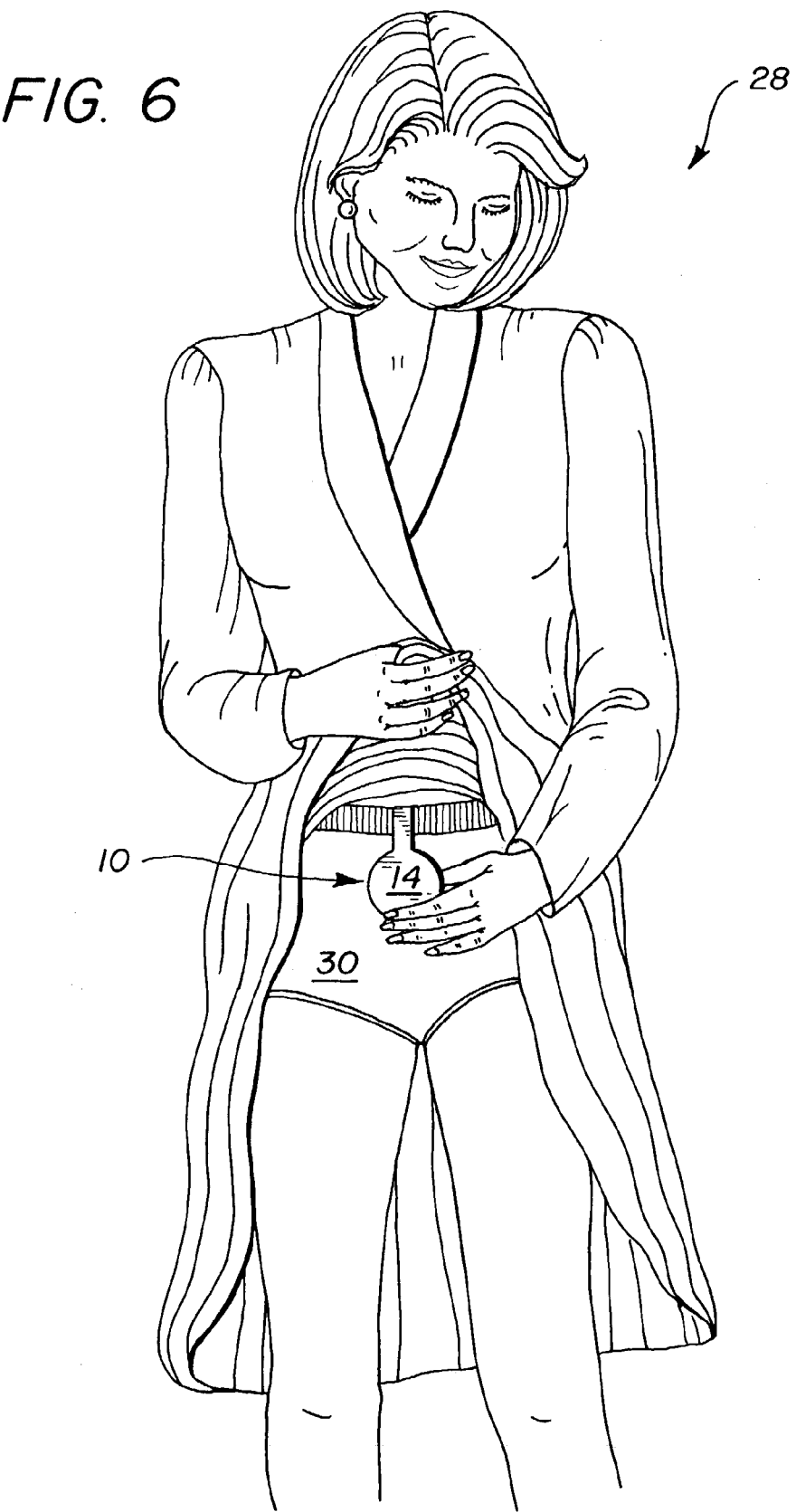
FIG. 6 shows a perspective view of a female wearing a reminder pad as in the invention.

FIG. 6 shows female user 28 attaching pad 10 to flyless female brief 30, and as is described above for a male user, pad 10 is positioned in the area of the groin. Reminder area 14 of pad 10 then serves the function of reminding individual 26 or 28 or a treatment provider to collect a specimen such as a urine sample or to perform a treatment such as to administer a topical agent or some other type of medication to that region of the body.

Pad 10 can be fabricated from any convenient material, the choice of which may depend on its relative cost, durability, workability, and so forth. A preferred such material is cardboard, for example a lightweight cardboard having a thickness in the range of from about 20 mils to about 100 mils.

Figure 1:
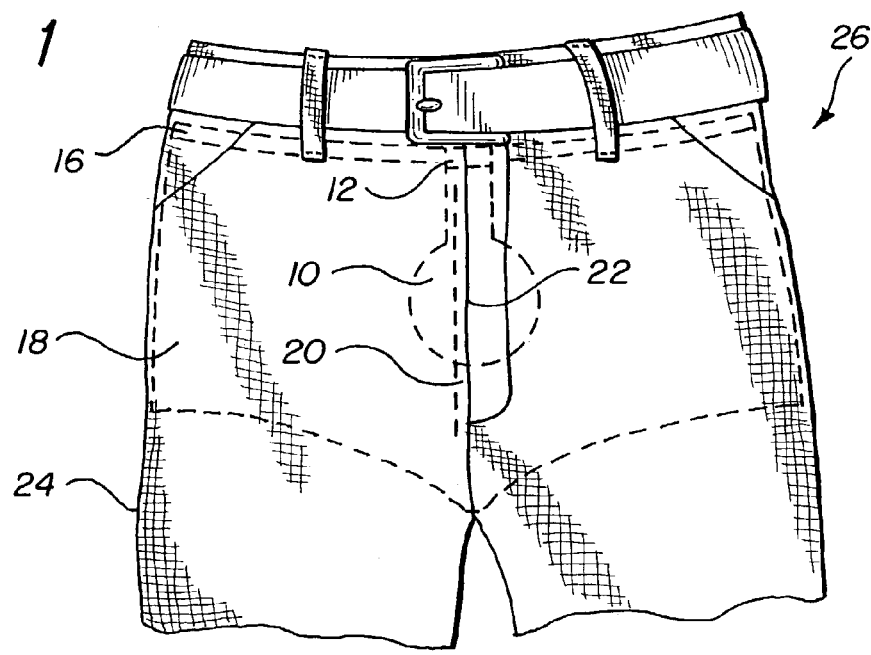
FIG. 1 shows a perspective, partially fragmentary view of an individual with a reminder pad (shown in phantom) attached to an undergarment (shown in phantom) as in the invention.

The size of pad 10 should be such that the wearer will encounter pad 10 and reminder area 14 in the course of performing a normal bodily function such as urinating and thereby serve as a tactile reminder to collect the specimen. Preferably, reminder area 14 has an area in the range of from about ½ to about 10 square inches. FIGS. 1 and 6 show pad 10 suspended from waistband 16 with reminder area 14 of sufficient size so that the male or female wearer will touch pad 10 on either male brief 18 or female brief 30 when preparing to urinate. In these embodiments, reminder area 14 has an area preferably in the range of from about 3 to about 10 square inches. FIG. 3 illustrates this type of pad 10 possessing a tennis racket-shape where substantially circular or oval reminder area 14 tapers into extending rectangular portion 12.

Figure 5:
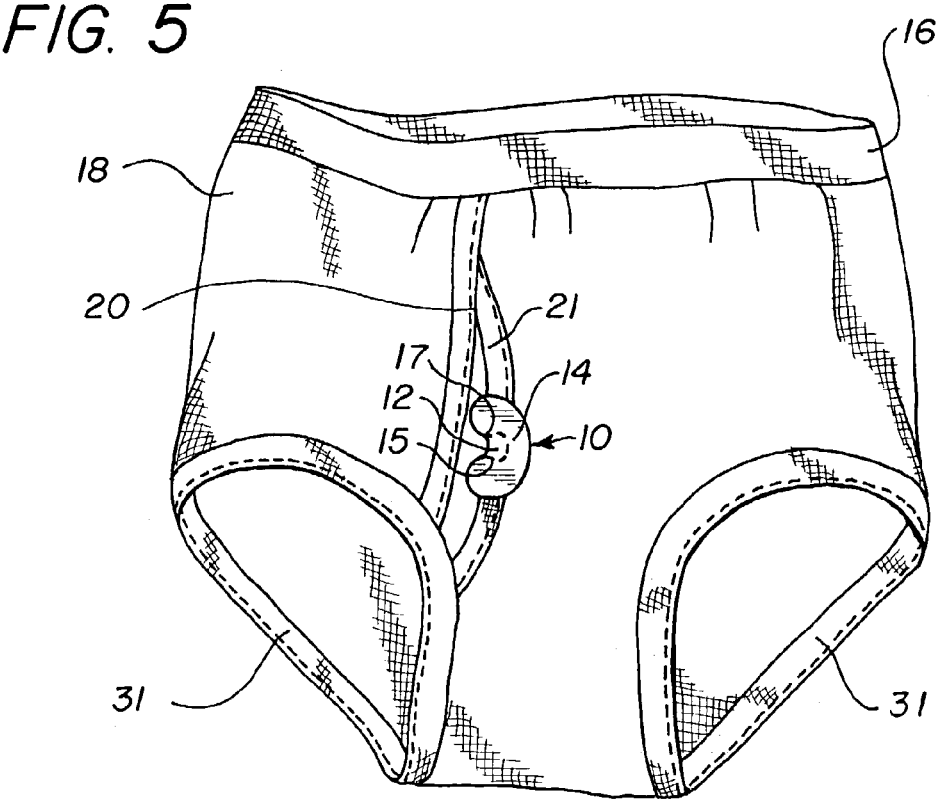
FIG. 5 shows a front elevational view of an undergarment with attached reminder clip as in the invention.

FIG. 5 shows pad 10 attached to vertical fold 21 of fly 20. In this embodiment, reminder area 14 preferably has an area in the range of from about ½ to about 2 square inches. A reminder pad of this size could similarly be attached at an appropriate location on female brief 30, and with either brief 18 or 30 pad 10 could optionally be attached to leg opening 31. When attached to the fly, the wearer upon preparing to urinate could opt to relocate it or push it aside instead of removing pad 10 and then having to reattach it.

Likewise, an appropriately sized and shaped pad 10 could be attached to the back of waistband 16 of brief 18 in the area of the wearer's buttocks, or elsewhere on brief 18, to remind the wearer in the course of performing a normal bodily function such as passing stool that must be collected, for example for a hemoccult, or administer a treatment at or near the site where pad 10 is so positioned.

Pad 10 as discussed above may be a clip, such as a one-piece foldable metal clip similar to a lapel badge or one having a double circle connected by a foldable bridge. Pad 10 may also be a modified safety pin presenting a nickel-size reminder area 14 when worn on brief 18 or 30. In another embodiment, pad 10 may be a metal nose clip on the outside of which is a metallic or plastic sphere serving as reminder area 14.

The invention also includes the method of an individual 26 or 28, or a treatment provider, encountering pad 10, being reminded by the presence of pad 10 to collect a specimen or conduct a treatment, and then collecting the specimen or performing the treatment.

The user, prior to the step of collecting the specimen or performing the treatment, may optionally either remove pad 10, reposition pad 10 as may be convenient, or remove the clothing on which pad 10 is secured.

As shown in FIG. 3, reminder area 14 of pad 10 is circular and as such is configured and sized to cover a sufficient portion of a desired area on a user's clothing or person such that the reminder function is effectuated while any resulting inconvenience or discomfort to the user is minimized. For example, as illustrated in FIG. 1 a male may select pad 10 having a size and shape that covers a substantial portion of fly 20. Pad 10 may also be positioned for convenience or comfort, for example off to one side or even underneath fly 20. The practice of the invention therefore includes the use of pads 10 of varying sizes and shapes, and the selection of the appropriate pad 10 to include in a specific collection or treatment kit or procedure may depend on factors such as the size of the user, the age of the user, and the area where pad 10 will be worn, to name but a few.

As alluded to in the preceding paragraph, the invention further includes providing to a health care provider or patient pad 10 as a component of or addition to a specimen collection or self-administered treatment kit, for example, a urine specimen collection kit or a hemoccult test kit. Thus, a urine collection kit as in the invention may include: a container for holding a collected urine specimen, for example a plastic jug having a capacity of from about one to two liters of fluid; optionally, an anti-bacterial agent or preservative in the container for maintaining the biological efficacy of the collected specimen; optionally, a set of written or printed instructions; and pad 10 which can either be included in the kit or provided separately as an addition to the kit. Although in the figures pad 10 is attached by means of tab 12, other means for attaching or securing pad 10 to brief 18 include an adhesive backing with or without a release sheet, VELCRO brand interlocking tape or the equivalent, buttons, snaps, and other fasteners well known in the art. The invention can also include the use of a separate fastening means, for example a safety pin, paper clip, or binder clip or the like.

The reminder system can serve both to remind the user to collect the sample themselves or if for some reason they are unable to do so then to remind a treatment provider such as a spouse, relative, or nurse, to do so.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for reminding an individual to collect a urine specimen, comprising the steps of:
   providing a reminder pad having a reminder area of a size such that the individual will discover the pad in the course of urinating, thereby serving as a reminder to collect the urine specimen;
   attaching the pad to a brief in the groin area of the individual, in a location where the pad will be encountered, and underneath an outer-garment whereby the pad is hidden from view when in normal use and whereby the individual when preparing to urinate will discover the pad and thereby be reminded to collect the urine specimen;
   discovering the pad when preparing to urinate;
   reminding the individual to collect the urine specimen when the individual discovers the pad; and
   collecting the urine specimen in a collection container.

2. A method as in claim 1, further comprising the step of providing the pad as part of a urine collection kit to a health care provider or to a patient.

3. A method as in claim 1, wherein the brief includes a fly having a vertical fold and the pad is attached to the vertical fold.

4. A method as in claim 1, wherein the pad includes a foldable or integral fold portion with which the pad is attached to the brief.

5. A method as in claim 4, further comprising the step of providing the pad as part of a urine collection kit to a health care provider or to a patient.

6. A method as in claim 4, further comprising the steps of: removing the pad.

7. A method as in claim 4, wherein the brief includes a fly and the attaching step positions the pad over at least a portion of the fly.

8. A method as in claim 7, wherein the pad is attached to a waistband of the brief.

9. A method as in claim 7, wherein the pad is attached to a leg opening of the brief.

10. A method as in claim 9, further comprising the step of: removing the pad.

11. A method as in claim 7, wherein the fly has a vertical fold, the reminder area of the pad has an area in the range of from about ½ to about 2 square inches, and the pad is attached to the vertical fold of the fly.

12. A method as in claim 11, further comprising the step of:
removing or relocating the pad.

13. A method as in claim 1, further comprising the step of: removing the pad.

14. The method of claim 1, wherein the pad is made of cardboard.

15. The method of claim 1, wherein the pad has a thickness of approximately 20 mils to approximately 100 mils.

16. A method for reminding an individual to collect a urine specimen, comprising the steps of:
(a) providing a reminder pad having:
  (i) a reminder area of a size such that the individual will touch and discover the pad in the course of urinating, thereby serving as a tactile reminder to collect the urine specimen; and
  (ii) a foldable or integral fold portion for attaching the pad to a brief and underneath an outer-garment whereby the pad is hidden from view when in normal use;
(b) attaching the pad to the brief with the foldable or integral fold portion, such that the reminder area is positioned over the groin and underneath an outer-garment whereby the pad is hidden from view when in normal use whereby the individual when preparing to urinate will touch and discover the pad and thereby be reminded to collect the urine specimen;
(c) touching and discovering the pad;
(d) removing or relocating the pad; and
(e) collecting the urine specimen in a collection container.

17. A method as in claim 16, further comprising the step of providing the pad as part of a urine collection kit to a health care provider or to a patient.

18. A method for reminding an individual to collect a urine specimen, comprising the steps of:
providing a reminder clip having a reminder area of a size such that the individual will discover the clip in the course of urinating, thereby serving as a reminder to collect the urine specimen;
attaching the clip to a brief in the groin area of the individual, in a location where the clip will be encountered, and underneath an outer-garment whereby the clip is hidden from view when in normal use and whereby the individual when preparing to urinate will discover the clip and thereby be reminded to collect the urine specimen;
discovering the pad when preparing to urinate;
reminding the individual to collect the urine specimen when the individual discovers the pad; and
collecting the urine specimen in a collection container.

19. A method as in claim 18, wherein the clip has a flared portion on each side of a tab, the brief has a fly having a vertical fold having two sides, and the clip is attached to the vertical fold such that the flared portions overlie both of said sides of the vertical fold.

20. A method as in claim 18, further comprising the step of:
removing or relocating the pad.

21. A method for reminding an individual to collect a urine specimen, comprising the steps of:
(a) providing a reminder pad having:
  (i) a reminder area of a size such that the individual will discover the pad in the course of urinating, thereby serving as a reminder to collect the urine specimen; and
  (ii) a foldable or integral fold portion for attaching the pad to a brief and underneath an outer-garment whereby the pad is hidden from view when in normal use;
(b) attaching the pad to the brief with the foldable or integral fold portion, such that the reminder area is positioned over the groin and underneath an outer-garment whereby the pad is hidden from view when in normal use whereby the individual when preparing to urinate will discover the pad and thereby be reminded to collect the urine specimen;
(c) discovering the pad; and
(d) collecting the urine specimen in a collection container.

* * * * *